United States Patent [19]

Soldin

[11] Patent Number: 5,322,772

[45] Date of Patent: Jun. 21, 1994

[54] RAPAMYCIN ASSAY

[75] Inventor: Steven J. Soldin, Washington, D.C.

[73] Assignee: Children's Research Institute, Washington, D.C.

[21] Appl. No.: 682,067

[22] Filed: Apr. 9, 1991

[51] Int. Cl.$^5$ .................... G01N 1/00; G01N 33/536; G01N 33/543; G01N 33/567

[52] U.S. Cl. .................... 435/7.9; 435/7.92; 435/7.8; 435/968; 436/178; 436/503; 436/518; 530/825

[58] Field of Search ............... 424/92; 435/7.92, 7.9, 435/7.93, 8, 21, 7.8, 968; 436/503, 178, 518; 530/825

[56] References Cited

FOREIGN PATENT DOCUMENTS 0041795 12/1981 European Pat. Off. .

OTHER PUBLICATIONS

Siekierka et al., *Nature*, 341:755 (Oct., 1989), "Acytosolic binding protein for the immunosuppressant FK506 has peptidyl-prolyl isomerase activity but is distinct from ayelophilin".

Harding et al., *Nature*, 341:758 (1989), Oct., "A receptor for the immunosuppressant FK506 is a cis-trans peptidyl-prolyl isomerase".

Bierer et al., *PNAS*, 87:9231 (1990), Dec. "Two distinct signal transmission pathways in Tlymphocytes are inhibited by complexes formed between an immunophilin and either FK506 or rapamycin".

Bronstein et al., "1,2-Dioxetanes, Novel Chemiluminescent Enzyme Substrates, Applications to Immunoassays", Journal of Bioluminescence and Chemiluminescence 4:99, 1989.

Williams, Curtis A. and Merrill W. Chase, eds., *Methods in Immunology and Immunochemistry*, vol. 1, New York:Academic Press, 1967, pp. 315-348.

Coligan, John E., et al., eds., *Current Protocols in Immunology*, New York:John Wiley & Sons, 1991, pp. 2.7.1-2.7.9.

Bedfnarczyk, B., S. J. Soldin, I. Gasinska, M. D. Costa, & L. Perrot, 1988, Improved Receptor Assay for Measuring Digoxin Activity Clin. Chem. 34:393-397.

H. Fretz et al., Rapamycin and FK506 Binding Proteins Feb. 13, 1991, J. Am. Chem. Soc.113:1409-1411.

M. Oellerich 1984 Enzyme-Immunoassay: A Review J. Clin. Chem.-Clin. Biochem 22:895-904.

*Protein purification method*, Harris et al., eds. IRL Press. 1989, p. 245.

Dumont, F. J. et al., *J. Immunol.*, 144:1418 (1990).

Bierer, B. E., et al., *Proc. Nat. Acad. Sci.*, 87:9231 (1990).

Schreiber, S. L., *Science*, 251:283 (1981).

Donnelly, J. G., et al., *FASEB J.*, 5:A730 (1991).

*Primary Examiner*—Esther L. Keppkinger
*Assistant Examiner*—Nancy J. Parsons
*Attorney, Agent, or Firm*—Foley & Lardner

[57] ABSTRACT

A competitive protein binding assay for rapamycin and biologically-active metabolites, derivatives and analogues thereof in blood and other biological fluids is disclosed, wherein the binding reagent is a specific rapamycin binding protein either substantially purified from the soluble cytoplasm of target cells of rapamycin action, particularly normal or transformed lymphocytes, freshly collected or in established cell lines, or synthesized by recombinant DNA techniques. Solution phase and solid state assay systems are disclosed.

14 Claims, 7 Drawing Sheets

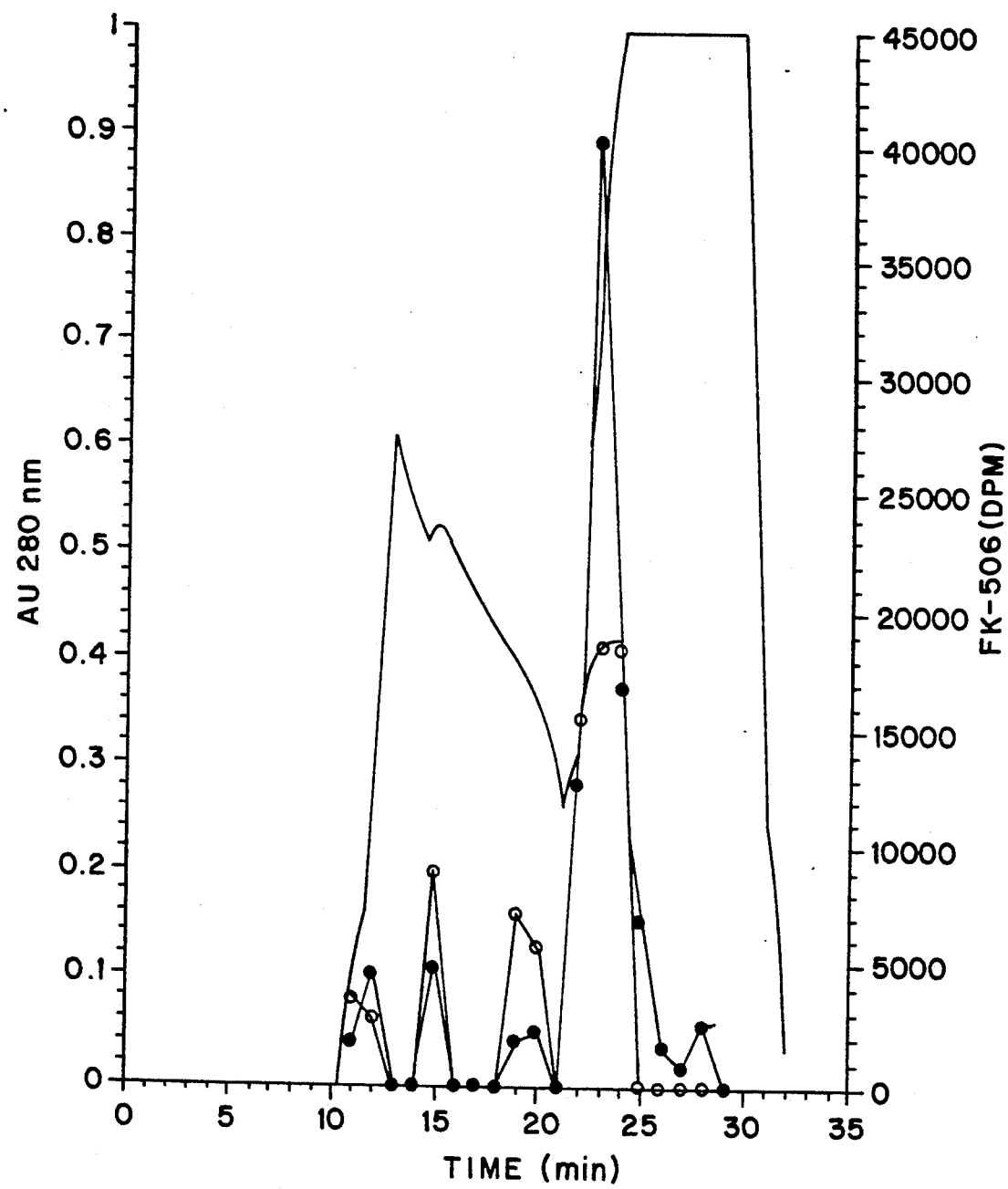
FIG. IA

RAPAMYCIN ASSAY

BACKGROUND OF THE INVENTION

1. Field of the Invention

The invention relates generally to assays for drugs in blood and other biological fluids. More particularly, it relates to isolated binding proteins for the immunosuppressive drug, rapamycin, and the use of these proteins in a quantitative competitive protein binding assay for rapamycin in blood and other biological fluids.

2. Description of the Background Art

Rapamycin ("RAP") is an antifungal macrocyclic-triene antibiotic extracted from *Streptomyces hygroscopicus* isolated from an Easter Island soil sample[1]. It is highly active against Candida species, especially *Candida albicans*. See, formula (1) below.

Early animal studies demonstrated that RAP is immunosuppressive; it totally prevented the development of experimental immunopathies and the formation of IgE-like antibody in rats[2].

Since these early reports, RAP has received little attention. However, interest in this molecule has recently been rekindled with the discovery that the macrolide antibiotic, FK-506, a product of *Streptomyces tsukubaensis*[3], bears structural similarity to RAP[4,5] (1).

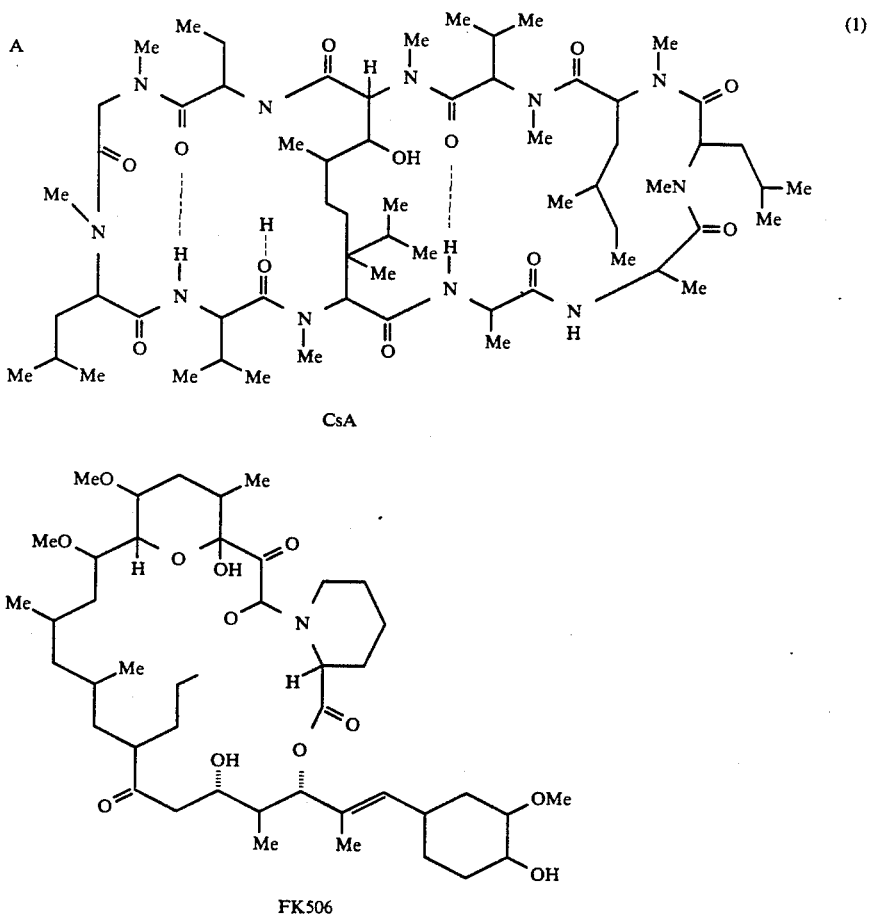

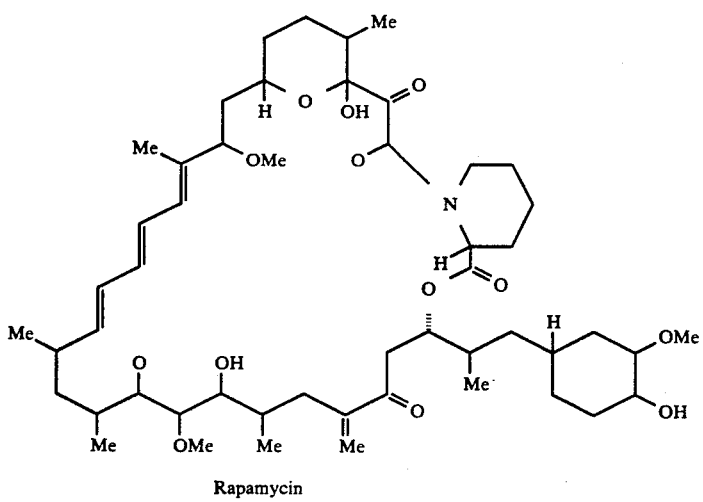

Rapamycin

FK-506 is capable of inhibiting immune responses with a potency some 100–500 fold greater than that of cyclosporine A[6] ("CsA"), currently the favored therapeutic agent for prevention of graft rejection after organ and bone marrow transplantation[7-9]. FK-506 has performed remarkably well in initial human clinical transplantation trials[10,11], despite reports of toxic effects in animals[12].

RAP inhibits T cell activation at concentrations comparable to those of the structurally related FK-506, yet with mechanisms reportedly strikingly different from those mediated by FK-506, and thus cyclosporine A[13]. A bright future for RAP as a clinically useful immunosuppressive agent is predicted.

The reportedly predominant cyclosporine binding protein is a cytosolic molecule of Mr 17,739 termed cyclophilin[14]. However, high specific binding of CsA to cytosolic proteins larger (e.g., 50–58 kDa) and smaller (e.g., 10–12 kDa) than cyclophilin have been identified in circulating and cultured lymphocytes, isolated, and used as a reagent in a competitive protein binding assay for CsA and its biologically active metabolites[15-17].

Binding of CsA to a 50 kDa protein was found to correlate well with a bioassay[17,18].

The reportedly predominant FK-506 binding protein in calf thymus, human spleen and the T cell line JURKAT, termed FKBP, is a heat stable protein of mass of about 10 kDa to 12 kDa[19-23]. However, I have identified and isolated specific receptor proteins for FK-506 in the range of 40 kDa to 60 kDa, particularly 51 kDa, and made the 51 kDa protein the basis of a competitive protein binding assay for FK-506 in biological fluids[24,25].

Both cyclophilin and FKBP are reported to exhibit peptidyl-prolyl isomerase activity[21,26]. This enzyme activity is inhibited by CsA and FK-506, respectively.

Recently, FKBP isolated from yeast, calf thymus and human T cells (JURKAT) has been shown to bind RAP with a Kd of about 0.2 nM, greater than the Kd (0.4 nM) for FK-506, and RAP is also reportedly a potent inhibitor of the aforementioned isomerase activity of FKBP[27].

There currently is no quantitative assay for RAP in blood and biological fluids suitable for use in a clinical setting. The only reported assay for RAP in serum or tissues is a microbiological bioassay[28]. Such assays are far too cumbersome, time consuming and expensive, and with far too little throughput of data, to be useful in a hospital clinical laboratory setting. The development of a suitable assay is critical to the clinical use of RAP.

The critical need in medicine for a rapid and specific assay for rapamycin and its biologically active metabolites, derivatives and analogues in blood and other biological samples is now filled by the competitive protein binding assay disclosed and claimed below.

SUMMARY OF THE INVENTION

A new method for the quantification of RAP and RAP-like functional activity in biological samples comprises a competitive protein binding assay (CPBA) wherein the binding reagent is a purified soluble binding protein isolated from mammalian cells.

It is thus an object of this invention to disclose purified water-soluble binding proteins specific for RAP and their biologically-active metabolites, derivatives and analogues for use in a competitive binding assay.

It is a further object to disclose aqueous solution-based and solid state-based competitive protein binding assays for RAP and its biologically-active metabolites, derivatives and analogues using the aforementioned purified binding protein.

It is yet another object of the invention to disclose labeled RAP molecules suitable for use in the competitive protein binding assay of the invention.

These and other objects of the invention will become apparent from the following description of the preferred embodiments thereof and from the claims.

DESCRIPTION OF THE DRAWINGS

FIG. 1A shows specific binding of labeled FK-506 to cytosolic proteins from JURKAT human T-lymphocytes in the absence (- o -) and presence (-o-) of unlabeled FK-506. Protein elution is shown by a dashed line.

DETAILED DESCRIPTION OF THE INVENTION

Figure 1B:
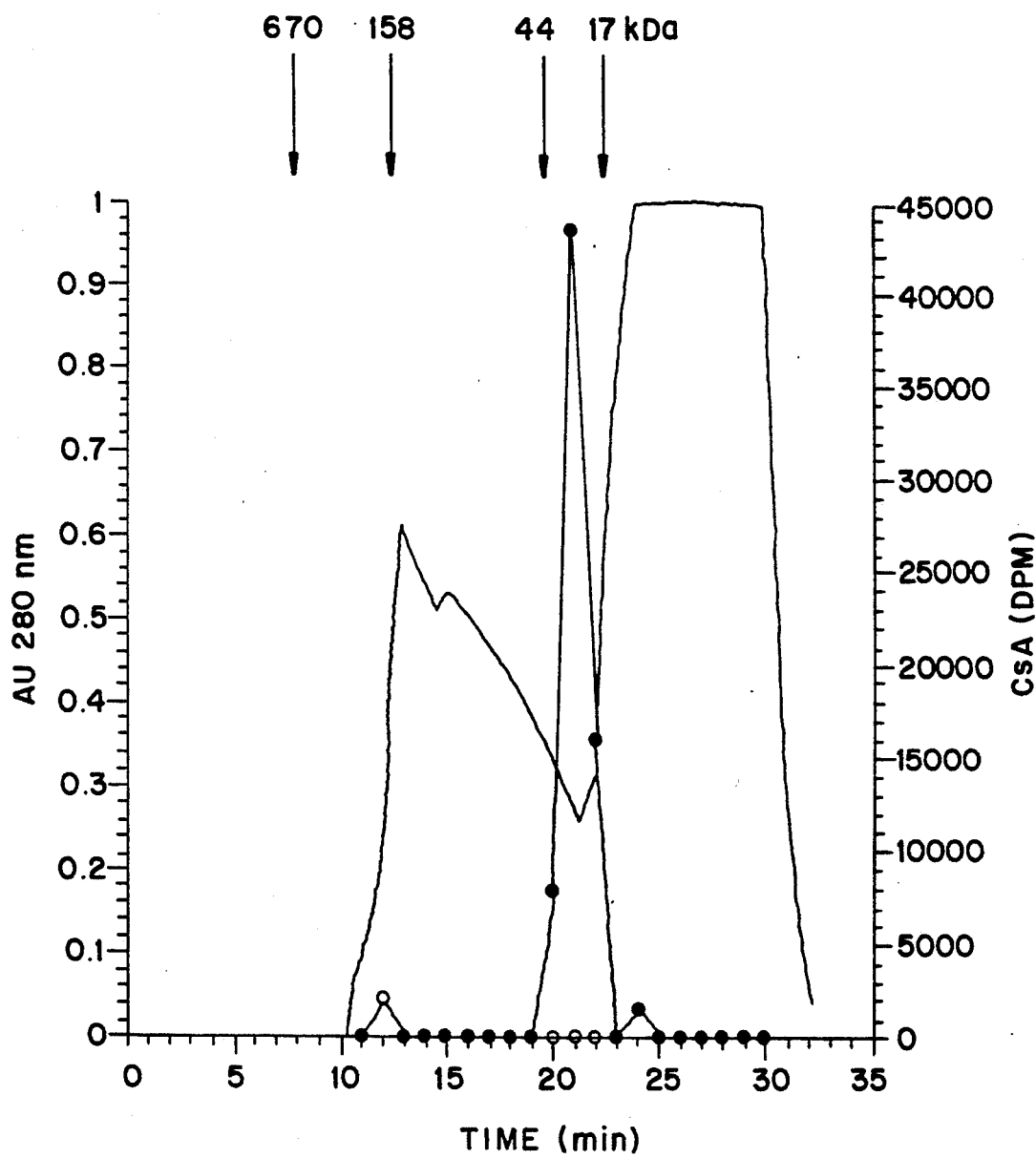
FIG. 1B shows the same system as in FIG. 1A, except that cyclosporine A was the ligand.

There is general agreement that the term "receptor" refers to a macromolecular protein or glycoprotein capable of recognizing and selectively binding with some ligand, and which, after binding the ligand, is capable of generating some chemical or physical signal that initiates the chain of events leading to the biological response attributed to that ligand[29].

It is thus an important aspect of this invention that the water-soluble binding proteins used as a reagent in the CPBA for RAP and its biologically-active metabolites, analogues and derivatives (hereinafter collectively referred to as RAP) exhibit several of the characteristics of a natural receptor protein, i.e., specific, saturable and reversible binding reflective of the first stage in the biological function of the drug.

We have previously identified and purified from the soluble cytoplasms (cytosols) of peripheral blood mononuclear leukocytes and a human T cell line (JURKAT) a 50-58 kDa protein capable of binding both CsA and FK-506. The Kd for CsA was 64 nM, and that for FK-506, 2 nM. The binding of CsA to this protein is inhibited by FK-506 in a dose-dependent manner. The binding characteristics of seven metabolites of CsA to this 50-58 kDa binding protein were quite distinct from those exhibited by their binding to cyclophilin, using $^3$H-cyclosporine A as the ligand and the LH-20 assay system[30]. M17, a major metabolite of CsA, had a bound 50% ($B_{50}$) value of 0.18, which compared well with the potency value of 0.19 relative to the parent drug using the mixed lymphocyte culture suppression assay as a model for allograft rejection.

We have now discovered that RAP also binds to this 50-58 kDa protein with a high affinity (Kd=0.1 nM), causing a displacement of $^3$H-dihydro FK-506, but not of $^3$H-cyclosporine A.

Water-soluble, specific binding proteins suitable for CPBAs carried out in accordance with this invention may be advantageously prepared from extracts of target tissues of RAP action, such as mammalian lymphocytes, including human or animal peripheral blood lymphocytes (PBL), primary mixed lymphocytes cultures, proliferating alloreactive T-cells propagated from organ transplant biopsies, and established cell lines such as the DQw1-specific alloreactive T-cell clone DB29[31], a transformed T-helper cell line (CEM), the interleukin-2-producing JURKAT human lymphocytic leukemia T-cell line (JURKAT 77.6.8)[19], and spleen.

As will be shown below, FK-506 and RAP, but not CsA and RAP, share binding sites. First, the two immunosuppressants each bind with high affinity to an isolated and purified 10 kDa-14 kDa JURKAT cytosol protein. Second, RAP also competes against labeled FK-506 for binding to all of the latter's binding proteins in this tissue, including a highly purified JURKAT cytosol protein of 50 kDa to 58 kDa size. RAP does not compete against CsA in binding of the latter to cyclophilin and to the 50 kDa to 58 kDa binding protein, although FK-506 and CsA bind to similar sites in the higher molecular weight protein.

It should be emphasized that the particular cellular source of the receptor protein used in the CPBA of the invention is not critical - the protein need only exhibit the binding properties of a physiological receptor detailed above.

Cells may be disrupted and the soluble proteins (cytosolic proteins) fractionated by art-recognized methods. Typically, lymphocytes are collected, washed and counted. Cells may be stored as a pellet at −70° C. until used or subjected to rapid freeze-thaw cycles just prior to use. Cells are thawed and homogenized with a Teflon or ground glass homogenizer at ice bath temperatures. Thoroughness of cell disruption can be tested by the trypan blue exclusion method. Homogenates are centrifuged in the cold under reduced pressure at least 20,000×g, preferably at least 100,000×g, for at least 0.5 hrs. The latter supernatant fluid, termed "S-100", which contains the RAP binding proteins, may be analyzed for protein content and binding activity, and is either used immediately or stored frozen at temperatures at or below about −20° C.

Cytosols can be used as such for the CPBA carried out in accordance with the invention. Preferably, however, RAP binding proteins are purified from the cytosol and concentrated prior to use. Such procedures reduce nonspecific binding background values and increase the accuracy and sensitivity of the method.

RAP binding protein can be partially purified from S-100 by heating the cytosol at about 55° C. for about 20 minutes. Precipitated proteins are removed by centrifugation, and represent extraneous non-RAP-binding proteins.

S100 cytosol, either before or after the heat step, can be fractionated by membrane molecular weight exclusion methods. For example, the protein solution may be centrifuged through a size exclusion membrane such as the 30 kDa cutoff Centriprep ™ Concentrator (Amicon Corp., Danvets, Ma.) to remove cyclophilin (about 17 kDa) and the 10 kDa–14 kDa RAP and FK-506 binding proteins; the 30 kDa and higher molecular weight RAP binding proteins will remain in the supernatant fluid. The >30 kDa fraction can be further fractionated by isoelectric focusing in, for example, a Rotofor ™ instrument (Bio-Rad, Richmond, Calif.).

At any stage, RAP binding proteins can be isolated by molecular sieve column chromatography. A preferred molecular sieve method uses a Beckman Instrument Co. HPLC instrument and a preparative BioRad Biosil SEC 125 column of appropriate dimension (see, Example 1, below). RAP binding protein can also be advantageously purified by cation exchange chromatography, e.g., by the weak cation exchange Beckman TSK CM-25W Spherogel. Hydrophobic interaction chromatographic matrices are also suitable for purifying the RAP binding protein according to this invention.

Any sequences or combinations of these fractionation systems can be used according to this invention as long as appropriate purifications are obtained. For example, purification by the sequence: S100 cytosol, heat purification, membrane sieving, isofocusing, molecular weight exclusion gel and weak cation exchanger is particularly preferred. For the purposes of the assay of this invention, a protein is deemed to be purified if, upon chromatography, a substantially single peak describes the elution pattern of both protein and binding activity, and if, upon SDS-PAGE, only one major protein band appears. Fractions of column eluates are collected, pooled, and concentrated in the cold. Concentrates are assayed for protein by any suitable method, including the Bradford BCA method. Concentrates are also tested for assay suitability by the CPBA.

It should be emphasized that a RAP binding protein used in accordance with this invention, may be prepared and purified by techniques other than by isolation from mammalian target cells. For example, the receptor protein may advantageously be synthesized by art-recognized recombinant DNA techniques.[32] In brief, cDNA coding for the receptor may be isolated from purified mRNA or from a cDNA cloning library, then cloned into cells, e.g., prokaryotic cells, to produce large amounts of the cDNA. An expression vector may be constructed containing the cDNA for a RAP binding protein, promoter and gene regulation sequences, a translation start codon, selectable markers, etc., and then inserted into prokaryotic or transformed eukaryotic cells. These cells will express the binding protein gene and secrete the protein in large quantities into the growth medium, from which it can be isolated by conventional methods.

For the purpose of a CPBA according to this invention, a protein fraction is deemed acceptable if: (1) the protein binds RAP to a statistically significant extent based upon the method of detection, e.g., radioactivity, fluorescence polarization, chemiluminescence and the like; (2) unlabeled and labeled RAP compete with each other for specific binding sites on the binding protein; and (3) the signal-to-noise ratio, i.e., the ratio of total binding to nonspecific binding (as these terms are defined below) is at least 1.1, preferably at least about 1.2. By these criteria, specific RAP binding proteins have been identified in the range of 1 kDa to 200 kDa, preferably between about 8 kDa and about 12 kDa, and between about 40 kDa and about 60 kDa; in the latter fraction, most preferably between about 50 kDa and about 60 kDa.

Gel electrophoresis and Western blot analyses may be used to monitor the purity of, and identify the binding protein throughout the stages of purification.

Labeled RAP is required for the CPBA carried out in accordance with this invention. Native RAP is available from Wyeth-Ayerst Pharmaceutical Co. and is soluble in aqueous amphipathic solvents, e.g., aqueous methanol. [$^3$H]-dihydro RAP can be prepared by art-recognized methods such as exposure of native RAP to tritium gas in the presence of a reducing agent, followed by purification by normal phase and reverse phase chromatography. Purification can be determined by TLC systems. One preparation of [$^3$H]-dihydro RAP, which was 98+% pure by three different TLC systems, had a specific activity of 13.6 Ci/mmol. The process adds one hydrogen and one tritium atom to the molecule. [$^3$H]-dihydro FK-506 and [$^3$H]-CsA are available from the Amersham Corp., Arlington Heights, Ill.

For fluorescence polarization detection methods suitable for use with, for example, the Abbott Laboratories, Inc. (Abbott Park, Ill.) TDX instrument, fluorophore-labeled RAP may be used. RAP may be labeled with a fluorophore by art-recognized methods.[33] Suitable fluorophores include fluorescein, europium and luciferin.

Chemiluminescent labels such as the water-soluble 1,2-dioxetane derivatives that release light energy upon cleavage with a hydrolytic enzyme[34,35] can be obtained from Tropix, Inc., Bedford, Ma. Chemiluminescence may also be the detection method when the RAP label is an enzyme that releases light upon addition of a substrate such as the aforementioned 1,2-dioxetanes.

The CPBA carried out in accordance with this invention can be performed by either solution phase or solid phase methods. The principle underlying both methods is the same. Briefly, a competition equilibrium is set up between a tracer amount of labeled RAP or other labeled ligand and unknown samples containing analyte RAP for binding to a fixed amount of the RAP binding protein described herein above. Following attainment of equilibrium or steady state binding, the amount of labeled RAP bound to the binding protein is determined. The amount of labeled RAP bound to the receptor will be reduced in the presence of unlabeled analyte RAP, and this reduction is proportional to the amount of unlabeled analyte present in the unknown sample. The quantitative relationship between the reduction of protein-bound label and the concentration of analyte in the unknown sample is determined by reference to a standard curve. To generate a standard curve, a fixed amount of binding protein is exposed to a fixed tracer amount of labeled RAP or other labeled ligand in the presence of zero-to-supersaturating concentrations of standard RAP. The supersaturating concentration is, ideally, several orders of magnitude greater than the association constant, $K_a$, of specific binding, and this fraction ("nonspecific binding," NSB) is assumed to be the same for all ligand concentrations, as nonspecific binding is assumed to be a linear function of ligand concentration.

For a solution phase standard curve assay, aliquots of an aqueous alcoholic (e.g., 50% ethanol in water) solution of unlabeled RAP are added to glass tubes, and the solvent evaporated, e.g., by a gentle stream of $N_2$ or in the cold under reduced pressure; the amount of RAP delivered ranges between zero and about 100,000 ng. For a solution phase CPBA of RAP in blood, whole blood is extracted with an amphipathic organic solvent, such as a lower alkanol (e.g., $C_1$ to $C_6$ straight or branched chain, primary, secondary or tertiary alcohol) or acetonitrile. "Amphipathic organic solvent" is intended to mean a liquid organic compound having both hydrophilic and hydrophobic properties. The precipitated proteins are removed by, e.g., centrifugation, and the extract containing RAP taken to dryness as described below. The residue to be analyzed is taken up in a small volume of a water/amphipathic organic solvent mixture, e.g., 1:3, and transferred to a reaction tube. To each tube is added a fixed tracer amount (e.g., 0.5 nM, 50,000–100,000 CPM) of labeled RAP in a small volume (e.g., about 50 μl) of stock solution. To each tube is then added a solution of binding protein in a small volume, e.g., about 100 μl–200 μl, of binding buffer, and the tubes incubated until equilibrium or steady state binding is reached, typically about 20 to 90 mins., at a slightly elevated temperature such as about 30° C. to about 40° C. The composition of the binding buffer is not critical. A preferred binding buffer is 20 mM Tris Buffer, pH 7.2, containing 5 mM 2-mercaptoethanol, 0.05% $NaN_3$ and 7.5% (v/v) fetal calf serum. To determine nonspecific binding (NSB), one set of tubes contains a large molar excess of unlabeled ligand, such as a 200-fold molar excess of unlabeled RAP delivered in a small volume, e.g., 50 μl.

At the end of the reaction period, for detection methods other than fluorescence polarization, it is necessary to separate protein-bound from free labeled RAP. Among the preferred methods in accordance with this invention are:

A. The contents of the reaction mixture are diluted with ice-cold buffer, preferably at neutral pH, the contents filtered through a glass fiber filter such as Whatman GF/B (Whatman Paper, Maidstone, England), and the filter washed with ice-cold buffer. The membrane retains the protein-bound labeled RAP compound.

B. This method is analogous to that of A, except that filtration is carried out on a microporous filter such as 0.22 μm nitrocellulose (Millipore Corp., Bedford, Ma.) prewashed with a solution of an inert protein, e.g., BSA or γ-globulin, to block nonspecific sites. The filter retains the protein-bound labeled RAP.

C. Following dilution of the reaction mixture with cold buffer, a suspension of polyethyleneglycol (MW 5,000 to 20,000), e.g., 1 ml of a 30 mg/ml suspension, plus a solution of a carrier protein, preferably delivering about 1 mg of carrier BSA or γ-globulin, are added, and the resulting suspension is mixed. The particles are collected by centrifugation; the pellet contains protein-bound labeled RAP.

D. Following dilution of the reaction mixture with cold buffer, a suspension of charcoal particles coated with a carbohydrate (e.g., dextran) or carrier protein (e.g., albumin or γ-globulin) is added to the tube, the suspension mixed thoroughly, then centrifuged in the cold to sediment the charcoal particles. The supernatant fluid will contain the receptor protein-bound labeled RAP.

E. The reaction mixture, typically a 100 μl aliquot run in duplicate, is poured onto a column of convenient dimension, such as 0.8×7.0 cm of a molecular sieve matrix such as LH-20 Sephadex (Pharmacia Fine Chemicals, Piscataway, N.J.). Washing the column with a small volume (e.g., about 0.5 ml of a buffer (e.g., phosphate-buffered saline, pH 7.4), will elute in the void volume, e.g., the first 2 ml, the protein-bound labeled RAP. LH-20 is a weakly hydrophobic matrix, and free RAP will be retarded in such a matrix.

Where a β-emitting radioactive tracer is employed with Methods A and B, each filter may be placed in a LSC vial, an aqueous-organic solvent phase combining scintillation system (e.g., PCSS, Amersham, Arlington Heights, Ill.) added, and the amount of radioactivity quantified. With Methods C and D, the pellet may be suspended in scintillant solution (e.g., PCSS) or dissolved in NaOH and diluted with scintillant solution, and then counted. With Method E, an aliquot of the void volume may be diluted in scintillant solution and counted. In all methods, when $^{125}$I is the tracer, filters, pellets or solutions containing labeled RAP are placed in counting tubes and counted in a γ-counter.

For quantification of labeled RAP by chemiluminescence when the reporter molecule is a chemiluminescent 1,2-dioxetane such as AMPPD or AMPGD (Tropix, Inc., Bedford, Ma.), with methods A and B filters may be placed on a sheet of blotting paper, and the filters soaked with a solution of the enzyme, e.g., alkaline phosphatase or galactosidase, that hydrolyses the 1,2-dioxetane and produces light. Filters may then be transferred to a piece of polyester film (e.g., Mylar), and then to a black box containing instant film, such as Type 612 Polaroid film. After exposure of the film to the emitted light, the dark image may be digitized using e.g., a black and white RBP Densitometer, Tobias, Assoc., Inc., Ivyland, Pa. In Method C, the pellet may be suspended in a buffer (pH 7-12) containing the appropriate enzyme and cofactors until maximum luminescence is attained, typically in 15-30 mins. at 30° C., and the luminescence read in a luminometer, e.g.,Turner 20E or Berthold Clinilumat instruments. In Method D, the void volume may be reacted with an appropriate hydrolytic enzyme until maximum luminescence is attained, typically in 15 to 30 mins. at 30° C., and the luminescence quantified in a luminometer. The methods are the same when RAP is labeled with the enzyme, such as alkaline phosphatase or α- or β-galactosidase except that the appropriate chemiluminescent substrate (AMPPD and AMPGD, respectively) is added to initiate the production of light.

The principle underlying fluorescence polarization-based assays is described by Robbins, et al.[36] and in the Abbott Laboratories 55 TDX Instruction Manual. In a fluorescence polarization CPBA carried out in accordance with this invention, fluorescein-RAP will not produce a polarized fluorescence signal as this molecule rotates freely, whereas the same molecule bound by a RAP binding protein will produce a signal as it is not free or as free, to rotate. Thus, receptor-bound and free fluorescein-RAP do not need to be physically separated in order to carry out this type of assay.

The assay system thus involves carrying out a CPBA with incubation of an initial sample containing standard or unknown RAP, labeled RAP (e.g., fluorescein-RAP), and water-soluble binding protein. The polarization intensity of the signal is inversely related to analyte concentration.[29] Therefore, a patient sample containing a low concentration of RAP analyte will, after equilibrium has been reached in the CPBA of this invention, have a high concentration of receptor protein bound tracer in the reaction mixture, and polarization will be high.

The fluorescence polarization CPBA for RAP carried out in accordance with this invention is readily adaptable to the Abbott Laboratories TDX System. In this adaptation, RAP standards, controls, and patient samples are placed in individual cartridges of the TDX instrument. A Metabolite Reagent Pack containing, in separate vials, a buffer-surfactant solution, a solution of RAP binding protein containing a protein stabilizer, fluorophore-labeled-RAP in a solution containing a surfactant and protein stabilizer, is placed in the instrument. Thereafter, in an automated series of steps, test samples are mixed with receptor protein and fluorescein-RAP, and the mixtures are incubated at 37° C. for a selected period until equilibrium binding is reached. Thereafter, samples are transferred to glass cuvettes, and the fluorescence polarization signal measured.

For presentation of CPBA data in accordance with this invention, standard curves are drawn for known RAP standard solutions by plotting $$[Bound_{(std)} - NSB/Bound_{(o\ std)} - NSB]100 \text{ vs } \log[RAP]$$

wherein $Bound_{(std)}$ is the total amount of labeled RAP bound at each concentration of standard RAP, $Bound_{(o\ std)}$ is the amount of labeled RAP bound in the absence of standard RAP, NSB represents nonspecific binding at each concentration of standard RAP determined by adding a large molar excess of unlabeled ligand, and [RAP] is the total concentration of rapamycin.

Thereafter, radioactivity, fluorescence polarization or chemiluminescence values for unknowns and controls are converted to

[Bound$_{(unk)}$/Bound$_{(o)}$]100 wherein Bound$_{(unk)}$ is the quantitative value of protein-bound and Bound$_{(o)}$ is the appropriate control value, by standard calculations. The calculated ratio is then referenced to the standard curve for estimation of the concentration of RAP or RAP-like molecules in the unknown samples.

Similar procedures and calculations are employed when FK-506 or CsA are the labeled ligands employed.

The CPBA of the invention can also be carried out in a solid state system. A supporting matrix, e.g., the bottom of wells of a microtitre plate or the walls of a tube or plastic beads is coated with RAP binding protein, and NSB sites are blocked by brief exposure to an inert protein, e.g., drug-free serum or serum albumin. An aliquot of a solution of labeled RAP is contacted with the coated surface with gentle shaking, and the solid surface washed with cold buffer solution, e.g., PBS at ice-bath temperatures. Thereafter, an aliquot of a patient sample containing RAP, its metabolites, or derivatives or analogues is contacted with a binding protein-coated surface with gentle shaking for a suitable period, e.g., 0 hrs. (control) to 16 hrs (analyte) in the cold. When equilibrium binding has been reached, the incubation fluid is removed, and the solid surface washed gently with cold buffer solution.

Protein-bound labeled RAP is removed from the solid surface by a surfactant solution or an alcohol, and the precipitated proteins removed by brief centrifugation. Thereafter the amount of label is quantified as described above for radioactively-labeled or chemiluminescence-labeled RAP. The calculations for standards and unknowns are carried out as above.

In order that those skilled in the art can more-fully understand this invention, the following examples are set forth. These examples are given solely for illustrative purposes, and should not be considered as expressing limitations unless so set forth in the appended claims.

EXAMPLE 1

Binding Competition between Rapamycin and FK-506

JURKAT human T-cells ($1.5 \times 10^9$) were cultured in RPMI 1640 medium supplemented with L-glutamine penicillin-streptomycin (Life Technologies, Gaithersburg, Md.), 2% fetal calf serum (MA Bioproducts, Walkersville, Md.), and insulin/transferrin/sodium selenate media extender (Boehringer Mannhelm, Indianapolis, Ind.) at 37° C. in 5% $CO_2$.

An S-100 fraction was prepared by pelleting the cells at low g-forces, washing the cells with RPMI 1640, resuspending the washed cells in 10 mM phosphate buffer (pH 6.8) containing 1 mM PMSF (Sigma, St. Louis, Mo.), disrupting the cells by four rapid freeze/thaw cycles in dry ice/acetone and a 40° C. water bath, and homogenizing the disrupted cells in a Potter-Elvehjem glass/Teflon TM homogenizer at high speed. The crude homogenate was centrifuged for 60 minutes at 100,000×g to obtain the cytosolic (S-100) fraction.

The S-100 fraction was further filtered (0.45 μm pore size membrane, Gelman Sciences), the filtrate (2.9 mg protein) passed through a 600×7.5 nun Bio-Sil-125 HPLC exclusion column at a flow rate of 1.0 ml/minute in 10 mM phosphate buffer, pH 6.8; protein elution was monitored at 280 nm. Fractions (1 ml) were collected and analyzed for binding of $^3$H-dihydro FK-506 using the previously described LH-20 assay, Donnelly et al., 1991, above, which is herein incorporated by reference. Specific binding was determined by assaying each fraction without (total binding) and with (specific binding) an excess of unlabeled FK-506.

Specific binding of 3H-dihydro FK-506 in the absence (- o -) and presence (-o-) of unlabeled FK-506, and protein elution (---) are shown in FIG. 1A. Several regions of minor binding were detected (12, 15 and 19 minutes), but the major binding peak (20-25 minutes) corresponded to a protein of 10-14 kDa based on Bio-Rad (Richmond, Calif.) molecular weight standards.

RAP (Kd 0.7 nM) was able to inhibit the binding of $^3$H-dihydro FK-506 to all fractions.

When the experiment was repeated with $^3$H-RAP and unlabeled RAP, the protein elution/specific binding profile was the same as that obtained in FIG. 1A, demonstrating that the 10–14 kDa protein also represents a major RAP binding protein, as found by others (See, Background section).

EXAMPLE 2

Rapamycin Binding to Cyclosporine a Receptor

The experimental conditions of Example 1A were repeated, except that $^3$H-cyclosporine A and unlabeled cyclosporine A were substituted for FK-506.

The data of FIG. 1B demonstrate that there are two binding proteins for cyclosporine A—the major one at 21–22 minutes (17 kDa, presumably cyclophilin) and a minor binding protein shown as a shoulder on the major peak at 20 minutes (50 kDa).

Rapamycin, even at 70 nM, did not affect the binding of cyclosporine A to either protein.

EXAMPLE 3

Specific Binding of Immunosuppressive Drugs to a Purified 58 kDa Cytosolic Protein from Lymphocytes The 58 kDa protein was purified from $1.4 \times 10^{10}$ human T-cells (JURKAT). The S-100 fraction (10 ml) was centrifuged at 2500×g for 1 hour at 4° C. in a 30 kDa Centriprep TM concentrator (Amicon Corp., Danvers, Ma.). The concentrate (1 ml) was diluted with 15 ml of 10 mM phosphate buffer, pH 6.8, and concentrated down to 5 ml. This step removed proteins of less than 30 kDa, i.e., cyclophilin and FKBP, from the S-100 fraction.

The >30 kDa protein solution was separated by preparative isoelectric focusing at 4° C. using a Rotofor TM (Bio-Rad, Richmond, Calif.) which contained a prefocussed solution of ampholytes (0.73% solids/vol. of pH 4–6 and 6–8, and 0.37% solids/vol. of pH 8–10; total volume was 50 ml. The cathode contained 0.1M $H_3PO_4$ and the anode 0.1N HCl. A 12 W constant power supply (Pharmacia 3000/150, Piscataway, N.J.) was used to focus the unit until constant voltage (450 v) was achieved. The solution was separated into 20 fractions, whose pH values were immediately determined and which were assayed for specific binding of 3H-labeled RAP, dihydro FK-506 and CsA using the LH-20 assay. The fraction and CsA drugs was refocused under the to both FK-506 and CsA drugs was refocused under the same conditions, using only the ampholytes contained in the 2.7 ml fraction (diluted to 55 ml with deionized water). Focusing was complete when a constant voltage of 2200 was reached.

The 20 fractions were assayed for drug binding as above. At pH 6.29, binding of $^3$H-CsA was inhibited by unlabeled FK-506 in the LH-20 assay. This fraction (3.02 mg in 2.7 ml) was chromatographed in a Bio-Sil-125 HPLC column at a flow rate of 1.0 ml/minute in 10 mM phosphate buffer, pH 6.8. Fractions representing proteins of 50–60 kDa were screened for binding to both FK-506 and CsA.

Binding fractions were probed and chromatographed on a Beckman TSK CM-25W Spherogel column (26×4.6 mm) at a flow rate of 0.5 ml/minute in 10 mM phosphate buffer, pH 6.8. Fractions containing binding activity were probed and used for binding assays.

Figure 2A:
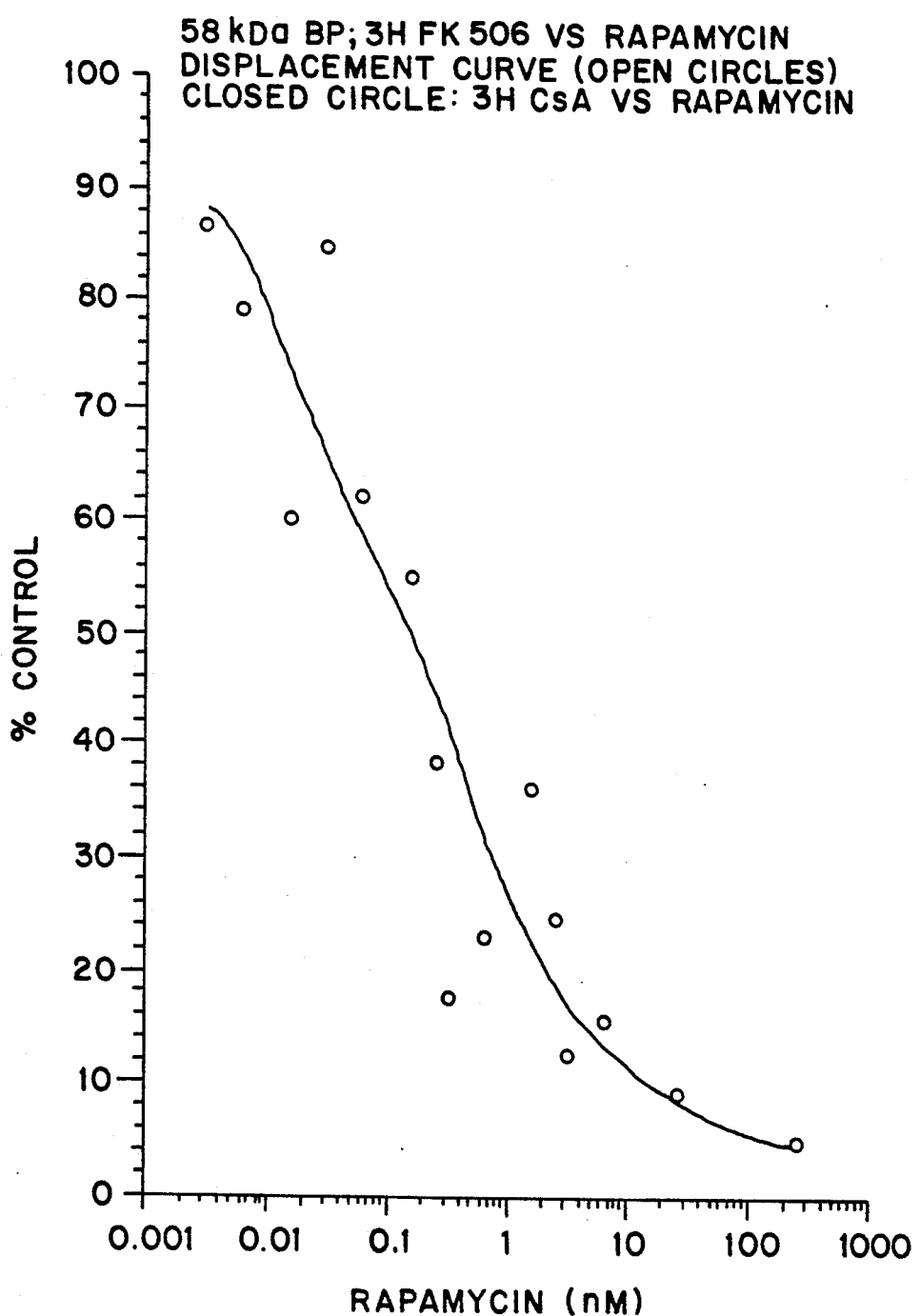
FIG. 2A shows the specific binding of labeled FK-506 to a substantially purified 58 kDa protein isolated from JURKAT S-100 in the absence and presence of unlabeled rapamycin.
Figure 2B:
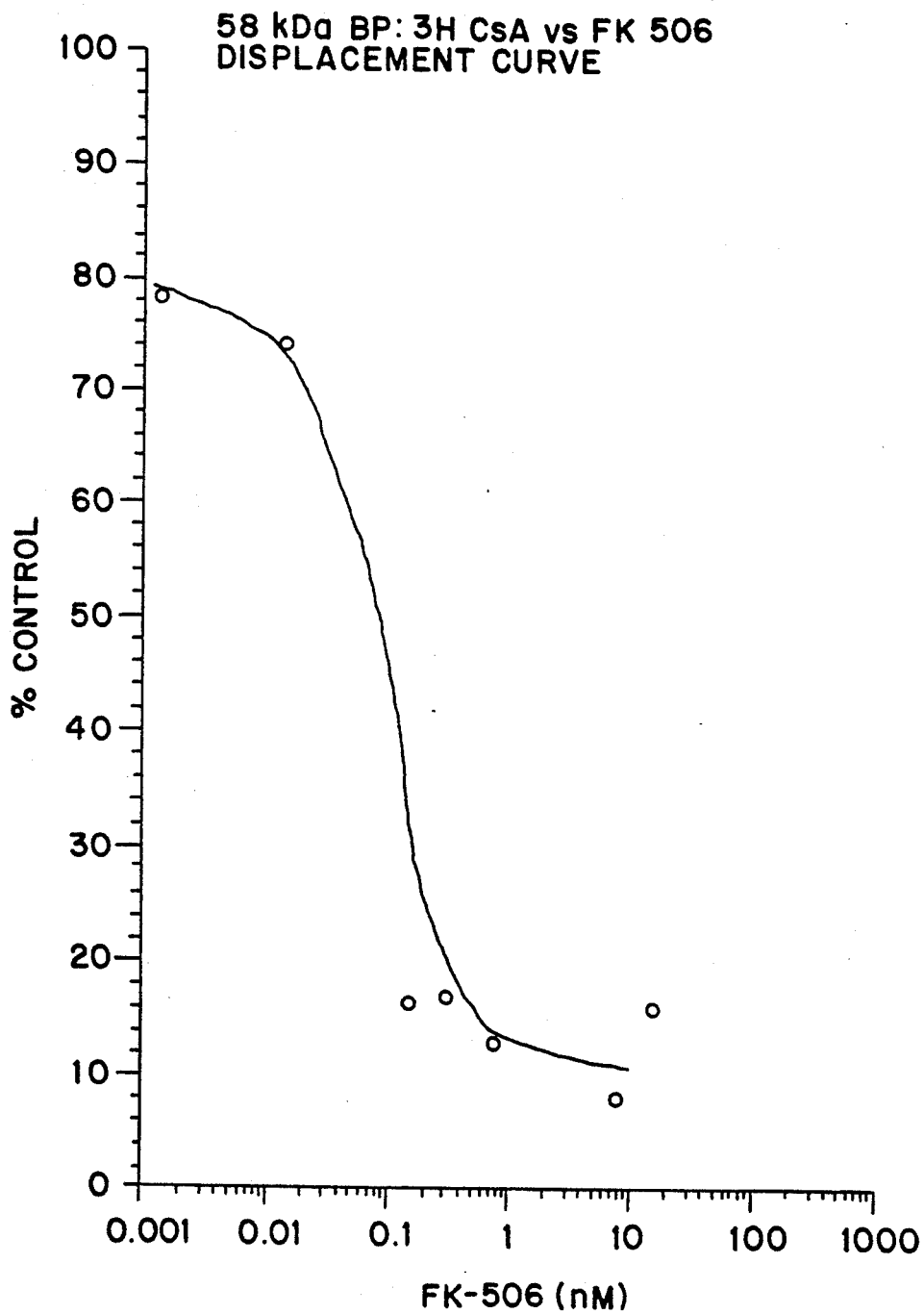
FIG. 2B shows the same system as in FIG. 2A, except that cyclosporine A was the labeled ligand.

The binding assay was the LH-20 assay of Example 1. In the FIG. 2A and FIG. 2B experiments, purified (Step V) 58 kDa binding protein was incubated for 15 minutes at 25° C. in 20 mM Tris HCl buffer, pH 7.4, 5 mM with $\beta$-mercaptoethanol and 2% with FCS, containing $^3$H-dihydro FK-506 or $^3$H-CsA and varying concentrations of unlabeled FK-506 or RAP.

It was found (FIG. 2A) that the specific binding of $^3$H-dihydro FK-506 to the purified 58 kDa protein was inhibited in a dose-dependent manner by RAP (0.005–500 nM). The $B_{50}$ value for RAP was 0.1 nM. The binding of $^3$H-CsA to this protein was unaffected by RAP even at concentrations of the latter of 300 nM.

When $^3$H-CsA was incubated with the purified 50-kDa protein and varying concentrations of FK-506 (FIG. 2B), binding of the former was inhibited in a dose-dependent manner ($B_{50} \approx 0.1$ nM).

These results suggest that the binding sites of RAP and FK-506 are closely related on the 58 kDa protein, whereas the binding site for CsA is distinct from that for RAP, but related to that for FK-506.

EXAMPLE 4

Binding of Radiolabeled Rapamycin to Jurkat Cytosol Proteins

Figure 3:
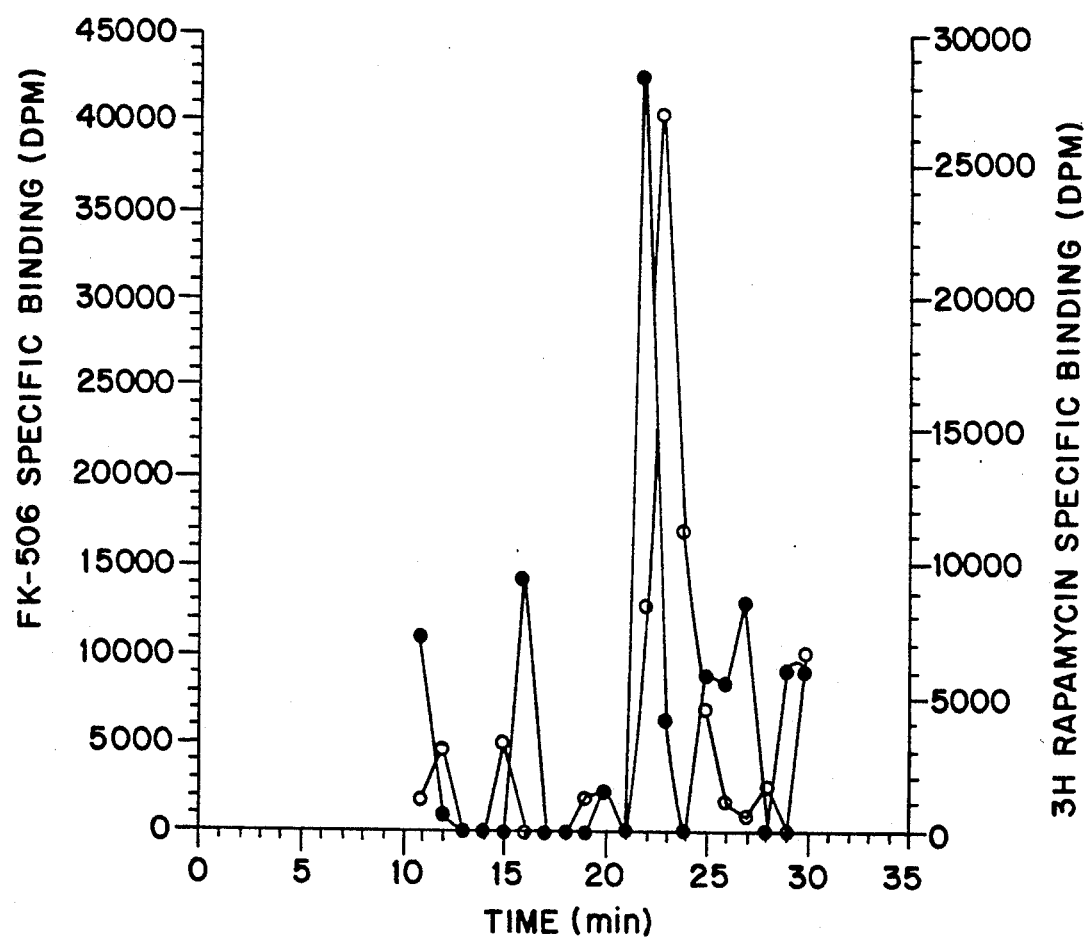
FIG. 3 shows the same system as in FIGS. 1A and B, except that labeled rapamycin was the ligand (-o-). FK-506 data from FIG. 1A is superimposed (-o-).

The procedure of Example 1, FIG. 1A, was carried out with $^3$H-RAP in order to determine specific binding. The binding $^3$H-RAP profile is shown in FIG. 3 (- ○ -), and that of $^3$H-dihydro FK-506 from Example 1A is superimposed (-○-). The retention times are slightly different due to changes in the column and in fraction collection methods between Examples 1A and 4. Nevertheless, it can be seen that the major binding peak for both drugs occurred between 20 and 24/25 minutes, corresponding to the 10–14 kDa binding protein. It is also clear that RAP also binds to lower (25–28 minutes) and higher (14–17 minutes) molecular weight proteins.

EXAMPLE 5

Figure 4:
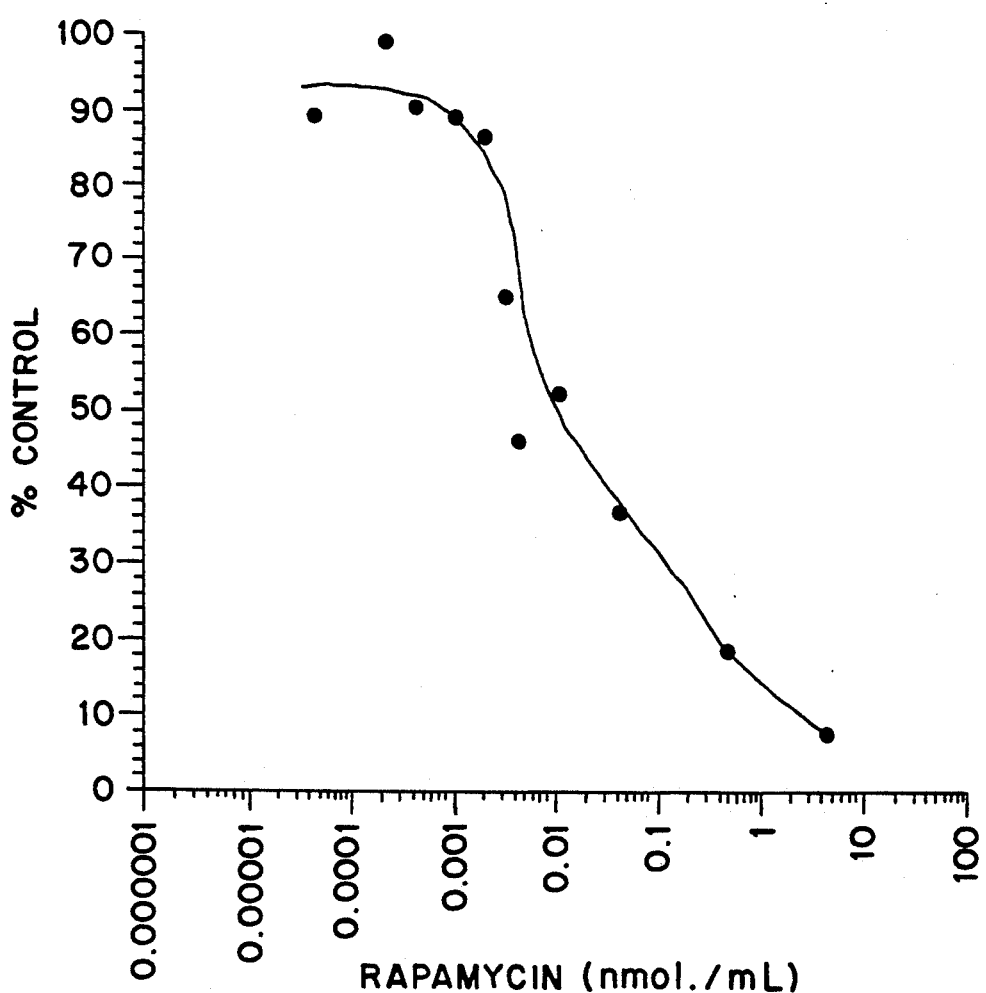
FIG. 4 shows a competition curve for rapamycin using a highly purified 58 kDa binding protein from JURKAT cytosol.

Competition Curve for Rapamycin Using a Highly Purified 58 kDa Binding Protein $^3$H-Rapamycin (2.95×10$^4$ μCi) was incubated with unlabeled RAP at concentrations of the latter of about 0.0001 to 10 nmol/ml using a 58 kDa protein purified from S-100 JURKAT cytosol (derived from 7.5×10$^8$ cells) by heating the S-100 fraction at 56° C. for 20 minutes, centrifuging off precipitated protein, then fractionating the supernatant fluid by BioSil125 HPLC size exclusion chromatography as described above. The LH binding assay was used for generating the competition curve of FIG. 4.

The data indicate that competition occurs at least over the concentrations range of about 0.001 and 5 nmol/ml RAP, with the useful (i.e., linear) range for use in CPBA of biological fluids ranging over 100-fold between about 0.005 and 0.5 nmol/ml.

EXAMPLE 6

Competition Curve for Rapamycin Using a Highly Purified 12 kDa Binding Protein

Figure 5:
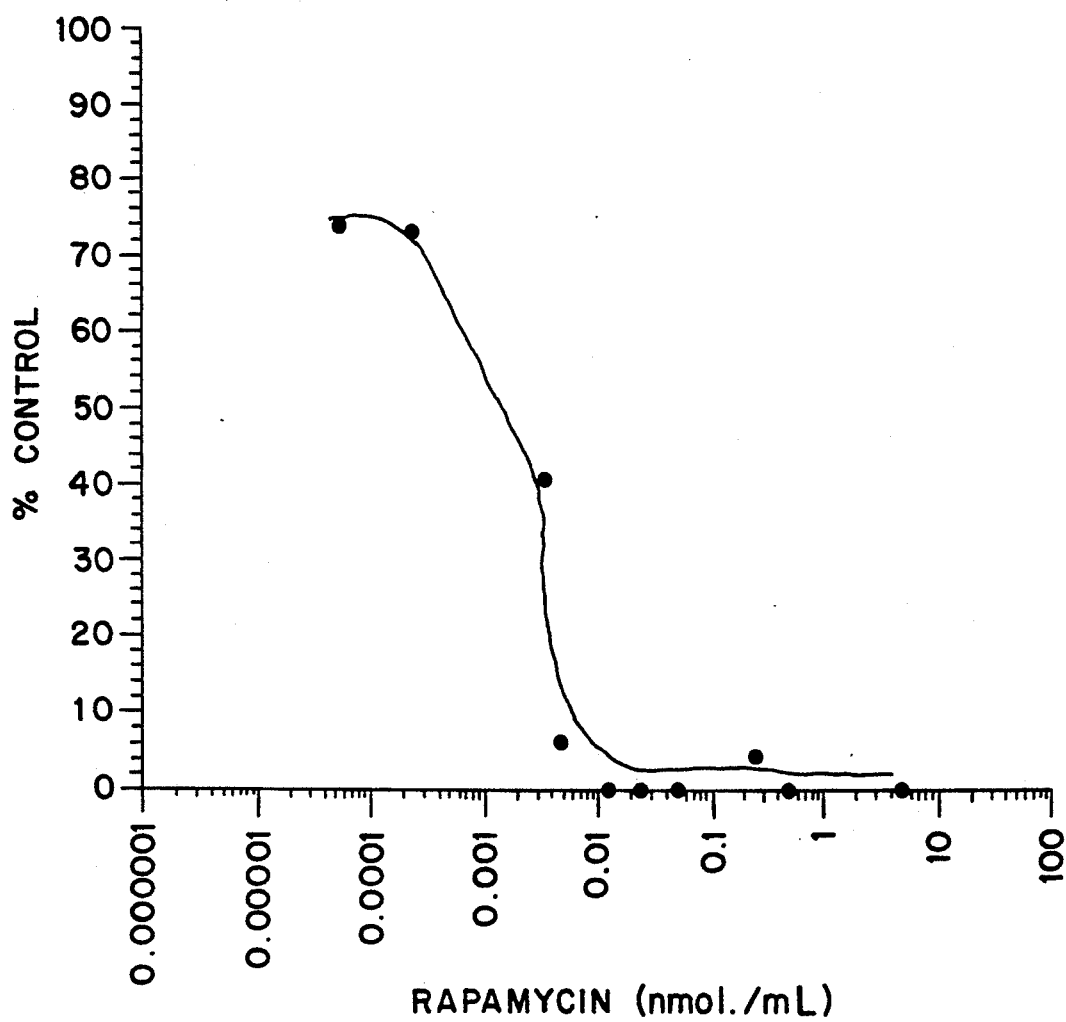
FIG. 5 shows the same system as in FIG. 4, except that a highly purified 12 kDa binding protein from JURKAT cytosol was used.

The experiment of Example 5 was repeated, but using a 12 kDa protein isolated from JURKAT cells and purified as above, as the binding reagent. The binding data are plotted in FIG. 5.

The competition range with the 12 kDa binding protein (about 0.005 to about 0.025 nmol/ml) was substantially smaller than that observed with the 58 kDa protein, and the useful range (0.005 to 0.05) is only about 10-fold, substantially less than that observed with the larger binding protein.

REFERENCES

1. Sehgal, S. N., et al., *J. Antibiot.*, 28:727 (1975).
2. Martel, R. R., *Canad. J. Physiol. Pharmacol.*, 55:48 (1977).
3. Kino, T., *J. Antibiot.* (Tokyo), 60:1249 (1987).
4. Findlay, J. A., *Canad. J. Chem.*, 28:579 (1980).
5. Tanaka, H., et al., *Transplant. Proc.*, 19:11 (1987).
6. Kino, T., et al., *J. Antibiot.*, 40:1256 (1987).
7. Showstack, J., et al., *N. Engl. J. Med.*, 321:1086 (1989).
8. Starzl, T. E., et al., ibid., p. 1092.
9. Oates, J. O., et al., ibid., p. 1725.
10. Starzl, T. E., et al., *Lancet*, ii:1000 (1989).
11. Starzl, T. E., et al., *J. Am. Med. Assoc.*, 264:63 (1990).
12. Thomson, A. W., *Immunol. Today*, 10:6 (1989).
13. Metcalf, S. M., et al., *Transplant.*, 49:798 (1990).
14. Handschumacher, R. E., et al., *Transplant.*, 46:298 (1988).
15. Soldin, S. J., et al., copending U.S. patent application Ser. No. 07/487,115.
16. Donnelly, J. G., et al., *Therap. Drug Monitor.*, 11:696 (1989).
17. Russell, R. R., et al., *Therap. Drug Monitor.*, in press, 1991.
18. Russell, R. L., et al., *Clin. Chem.*, 36:987 (1990).
19. Siekierka, J. J., et al., *J. Immunol.*, 143:1580 (1989).
20. Harding, M. W., et al., *Nature*, 341:758 (1989).
21. Siekierka, J. J., et al., ibid., p. 755.
22. Maki, N., et al., *Proc. Nat'l Acad. Sci. U.S.A.*, 87:5440 (1990).
23. Siekierka, J. J., EPO 379342, Jul. 25, 1990.
24. Soldin, S. J., et al., copending U.S. patent application Ser. No. 07/521,074.
25. Palazynski, E., et al., *Clin. Biochem.*, 24:63 (1991).
26. Fischer, G., et al., *Nature*, 337:476 (1989).
27. Bierer, B. E., et al., *Proc. Nat'l Acad. Sci. U.S.A.*, 87:9231 (1990).
28. Sehgel, S. N., et al., EPO 041795, Dec. 16, 1981.
29. Blecher, M., et al., *Receptors and Human Disease*, Williams & Wilkens, Baltimore, 1981, Chapter 1.
30. Donnelly, J., et al., *Clin. Blochem.*, 24:71 (1991).
31. Zeevi, A., et al., *J. Immunogenet.*, 12:17 (1985).
32. Old, R. W., et al. "Principles of Gene Manipulation," 3 ed., Blackwell Scientific Publications, Boston, 1985, Chapters 1–12; Maniatis, T., et al., "Molecular Cloning: A Laboratory Manual," Cold Spring Harbor Laboratory, N.Y., 1982, Chapters 6–12.

33. Mahoney, W. C., et al., U.S. Pat. No. 4,427,035, issued Feb. 23, 1988.
34. Bronstein, I. Y., et al., *J. Biolumin. Chemilumin.* 2:186 (1988).
35. Voyta, J., et al., *Clin. Chem.*, 34:157 (1988).
36. Robbins, B. A., et al., *J. Clin. Lab. Anal.*, 2:62 (1988).

I claim:

1. A protein binding assay method for analyte rapamycin or its biologically active metabolites contained in a fluid sample, comprising the steps of:
   a) contacting said fluid sample with a purified rapamycin binding protein of molecular weight of about 50-60 kDa;
   b) detecting the binding of said analyte in said fluid sample with said binding protein;
   c) quantifying the amount of said analyte bound to said binding protein; and,
   d) relating the quantified amount of analyte binding to the concentration of said analyte in said fluid sample.

2. A method of claim 1, wherein said fluid sample comprises an extract of a biological fluid sample.

3. A method of claim 2, wherein said extract is produced by contacting said biological fluid sample with an organic solvent in which said analyte is substantially soluble.

4. A method of claim 1, wherein said purified rapamycin specific binding protein of 50-60 kDa molecular mass is produced by a process comprising the steps of (i) centrifuging disrupted, normal or transformed tissue or cells so as to produce a cytosolic fraction containing a mixture of water-soluble proteins; and (ii) fractionating said cytosolic fraction so as to produce a purified rapamycin specific binding protein of molecular mass about 50-60 kDa molecular mass.

5. A method of claim 1, wherein said quantifying comprises the steps of (i) setting up a binding equilibrium reaction between said analyte and a tracer amount of a labeled rapamycin for binding to said purified binding protein; and (ii) determining the amount of said analyte in said fluid sample from the reduction in binding of said labeled rapamycin to said binding protein due to the presence of said analyte in said fluid sample.

6. A method of claim 5, wherein said reaction is carried out in free solution.

7. A method of claim 5, wherein said reaction is carried out on a solid surface.

8. A method of claim 7, wherein said solid surface is coated with said purified binding protein.

9. A method of claim 5, wherein said tracer comprises a radioactive atom, a fluorophore, a chromophore, an enzyme or a chemiluminescent molecule.

10. A method of claim 1, wherein said quantifying comprises fluorescence polarization in the presence of a fluorophore-labeled rapamycin.

11. A mercantile kit comprising:
   a) a given amount of a purified rapamycin specific binding protein of molecular weight of about 50-60 kDa.
   b) a given amount of a reference rapamycin; and, optionally,
   c) labeled rapamycin.

12. A kit of claim 11, wherein said binding protein is in solution.

13. A kit of claim 11, wherein said binding protein is in powder form.

14. A kit of claim 11, wherein said binding protein is in the form of a coating on a solid surface.

* * * * *